United States Patent
Wollmann et al.

(10) Patent No.: US 10,605,712 B2
(45) Date of Patent: Mar. 31, 2020

(54) ASSEMBLY FOR DETERMINING THE PERMEATION RATE OF A SAMPLE

(71) Applicant: FRAUNHOFER-GESELLSCHAFT ZUR FOERDERUNG DER ANGEWANDTEN FORSCHUNG E.V., Munich (DE)

(72) Inventors: Philipp Wollmann, Dresden (DE); Wulf Graehlert, Dresden (DE); Florian Gruber, Dresden (DE)

(73) Assignee: FRAUNHOFER-GESELLSCHAFT ZUR FÖRDERUNG ANGEWANDTEN FORSCHUNG E.V., Munich (DE)

( * ) Notice: Subject to any disclaimer, the term of this patent is extended or adjusted under 35 U.S.C. 154(b) by 32 days.

(21) Appl. No.: 15/746,884

(22) PCT Filed: Jul. 18, 2016

(86) PCT No.: PCT/EP2016/067019
§ 371 (c)(1),
(2) Date: Jan. 23, 2018

(87) PCT Pub. No.: WO2017/013050
PCT Pub. Date: Jan. 26, 2017

(65) Prior Publication Data
US 2019/0178777 A1    Jun. 13, 2019

(30) Foreign Application Priority Data

Jul. 23, 2015 (DE) .................. 10 2015 213 974

(51) Int. Cl.
*G01N 15/08* (2006.01)
*G01N 21/17* (2006.01)
(Continued)

(52) U.S. Cl.
CPC ......... *G01N 15/0826* (2013.01); *G01N 15/08* (2013.01); *G01N 2015/0846* (2013.01)

(58) Field of Classification Search
CPC .... G01N 15/00; G01N 15/08; G01N 15/0826; G01N 21/00; G01N 21/17; G01N 21/78; G01N 21/81; G01N 2015/0846
See application file for complete search history.

(56) References Cited

U.S. PATENT DOCUMENTS 3,902,068 A * 8/1975 Wood .................. G01N 15/08
250/343
5,381,228 A    1/1995 Brace
(Continued)

FOREIGN PATENT DOCUMENTS

EP         2153201 A2 *  2/2010  ............. G01N 21/05
WO    WO 2010/019515 A2    2/2010
(Continued)

OTHER PUBLICATIONS

Giovanni Nisato et al., "Experimental comparison of high-performance water vapor permeation measurement methods", Organic Electronics 15 (2014) 3746-3755.
(Continued)

*Primary Examiner* — Nguyen Q. Ha
(74) *Attorney, Agent, or Firm* — Jacobson Holman, PLLC.

(57) ABSTRACT

The invention relates to an assembly for determining the permeation rate of a sample for at least one permeate, in particular water vapor, wherein multiple detectors are arranged in a row or in a row and column arrangement for the spatially resolved spectral analysis of electromagnetic radiation within a wavelength interval. The detectors are connected to an electronic evaluation unit and are arranged
(Continued)

such that electromagnetic radiation emitted from a broadband radiation source is incident on the detectors either after being reflected by the surface of the sample, by a layer formed on the sample, or by the surface of a layer within the sample, and/or after passing through a sample which is transparent to the electromagnetic radiation. The irradiation is carried out such that a homogeneous intensity of the electromagnetic radiation is maintained on a surface, by means of which the electromagnetic radiation is reflected or through which the radiation is transmitted. The electronic evaluation unit is designed such that the detector measurement signals detected in a spatially- and wavelength-resolved manner can be detected within a wavelength interval for individual location points which are arranged on a specifiable surface of the sample. Each of the measurement signals detected at multiple positions are assigned to a sub-region of the detected surface (hypercube), and a data reduction process is carried out for all of the detected surface sub-region measurement signals which are detected in a wavelength-resolved manner, wherein informative features are selected and can be used together with a previously ascertained regression model, which is stored in an electronic storage device, in order to draw a conclusion regarding a corresponding permeation rate, said regression model being generated using the feature sets, which are obtained analogously, of samples with permeation rates which have been ascertained using another measurement method with a higher degree of measurement precision.

9 Claims, 1 Drawing Sheet

(51) Int. Cl.
  *G01N 21/78* (2006.01)
  *G01N 21/81* (2006.01)

(56) References Cited

U.S. PATENT DOCUMENTS

2010/0273209 A1* 10/2010 Eden .................... B01L 3/5082
  435/39
2013/0312491 A1* 11/2013 Beese ................ G01N 15/0826
  73/38

FOREIGN PATENT DOCUMENTS

| WO | WO-2012033648 A2 * | 3/2012 | ............. G01J 3/021 |
| WO | WO 2012/041945 A1 | 4/2012 | |
| WO | WO 2014163039 A1 | 10/2014 | |

OTHER PUBLICATIONS

Dr. Wulf Grählert, "Prozessüberwachung und Sensorik—der Qualität Verpflichtet", Fraunhofer IWS Jahresbericht 2014.
Philipp Wollmann; "Spektroskopie in neuen Dimensionen", Optische Systeme.

* cited by examiner

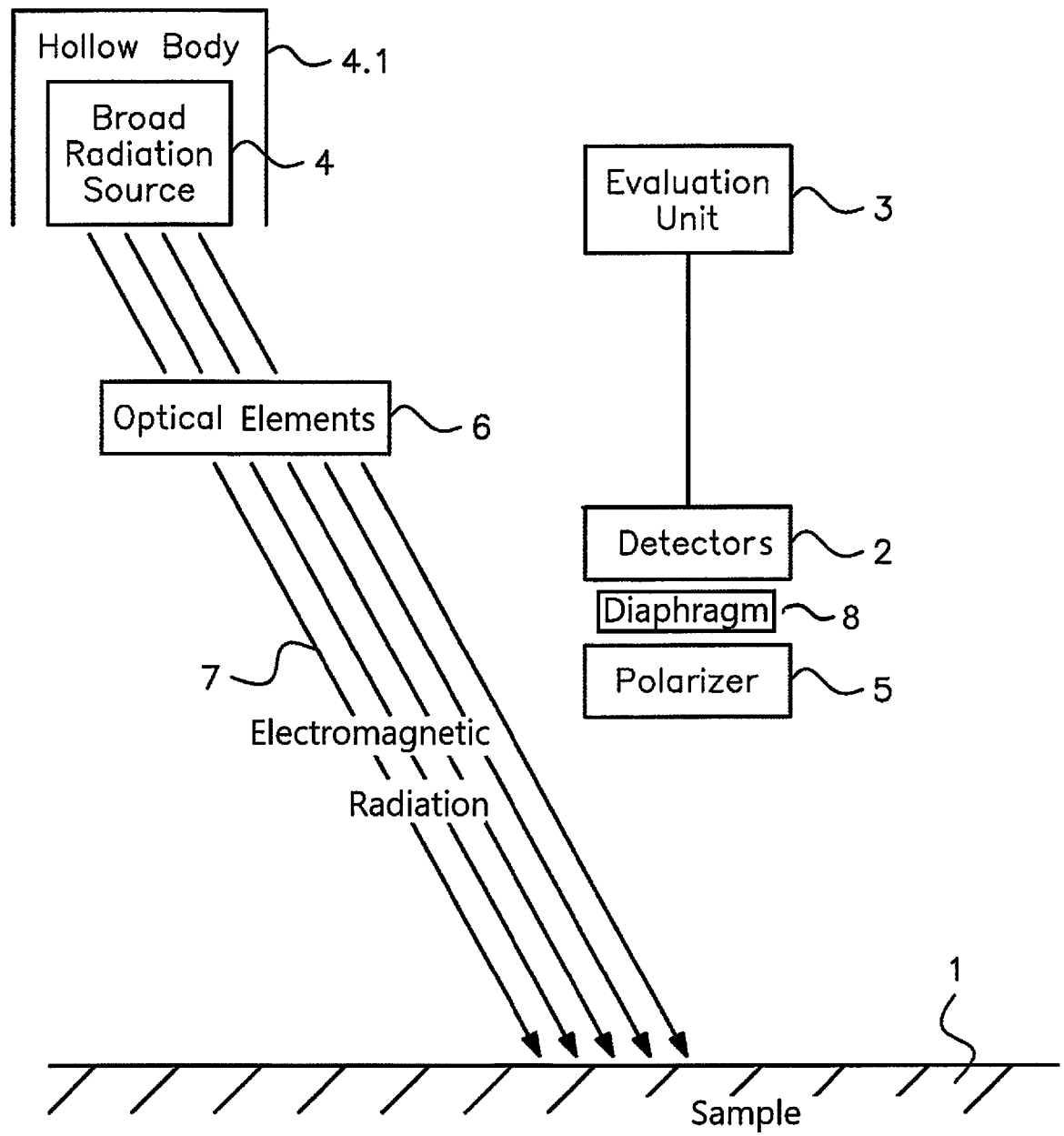

ASSEMBLY FOR DETERMINING THE PERMEATION RATE OF A SAMPLE

The invention relates to an assembly for determining the permeation rate of a sample for a permeate. The permeate should in particular be water vapor. Investigations can, however, also be carried out with it for oxygen, carbon dioxide, or methane as permeates. Samples can here be formed from barrier materials for the respective permeates.

It has previously been customary to determine permeation rates in apparatus directly, i.e. using the measurement of the gas or vapor permeated through the sample. A respective sample is arranged between two chambers here. A permeate to be investigated is contained in one chamber. A time-resolved detection of the permeate permeated through the sample takes place in the other chamber. The detection here takes place using a sensor that is highly sensitive for the permeate. In addition to coulometric sensors, spetrometers are also frequently used while utilizing known absorption bands of the respective permeate to quantify the permeate. The permeation rate (water vapor transmission rate—WVTR in $g/m^2/d$) can be determined therefrom.

A sufficiently high determination accuracy can be achieved using the known procedures. However, since barrier samples by their nature have a very good barrier effect, a substantial time effort is required for this conventional direct determination. A determination can here last several days up to weeks—depending on the barrier effect of the sample.

It is therefore the object of the invention to specify possibilities for the determination of permeation rates at samples that produce results having a sufficient accuracy in a considerably shortened time and that can thus even be used for an inline measurement in barrier production processes.

This object is achieved in accordance with the invention by an assembly having the features described below. Advantageous embodiments and further developments of the invention can be realized using features additionally designated below.

The assembly in accordance with the invention for determining the permeation rate of a sample has a plurality of detectors that are configured for a spatially resolved spectral analysis of electromagnetic radiation within a wavelength interval. These detectors are arranged for this purpose in a row arrangement or in a row and column arrangement. The detectors are connected to an electronic evaluation unit and are arranged such that electromagnetic radiation emitted by a broadband radiation source impacts the detectors either after reflection at the surface of the sample or at a layer formed on the sample and/or after the irradiation of a sample transparent for the electromagnetic radiation. The irradiation takes place here such that a homogeneous intensity of the electromagnetic radiation is observed on a surface from which the electromagnetic radiation is reflected or which is transmitted by the surface. The respective surface to be detected simultaneously should therefore be irradiated at a homogeneous intensity. In the broadband irradiation, electromagnetic waves that lie within a wavelength interval are directed to the respective surface of the sample that is to be investigated.

BRIEF DESCRIPTION OF THE DRAWING

FIG. 1 is a schematic representation of an arrangement embodiment according to the invention.

As exemplified in FIG. 1 a broadband radiation source (4) arranged inside a hollow body (4.1) emits electromagnetic radiation (7) directed as a beam by an optical element (6) at a sample surface (1). A detector (2) connected to an evaluation unit (3) is impacted by the beam of electromagnetic radiation after reflection at the sample surface and alignment by a polarizer (5). A diaphragm (8) arranged in front of the detector in the path of the beam of electromagnetic radiation avoids the incidence of scattered electromagnetic radiation.

The electronic evaluation unit is configured such that the measured signals detected by the detectors with spatial and wavelength resolution within a wavelength interval can be associated with a specific wavelength range and with an individual local point within a predefinable part region of the sample surface.

The totality of the intensities detected with wavelength resolution at all the local points of the respective sample surface forms a three-dimensional data structure comprising one dimension with wavelength resolution and two dimensions with spatial resolution (hypercube).

A data reduction for all measured signals of the part region detected with wavelength resolution should then be able to be carried out in which significant features are selected and the feature set resulting therefrom is subjected to a regression process using a regression model that is stored in an electronic memory and that was determined using feature sets that were determined earlier at samples whose permeation rates, in particular the water vapor transmission rates, were determined using a different measurement process that has higher measurement accuracy, whereby a statement can be derived on the permeation rate of the respective part region of the sample, with at least one part region being used to evaluate the permeation rate of the sample.

A sample investigated using the method in accordance with the invention should belong to the same sample class that should have a comparable structure or composition with those that had been determined beforehand using a different measurement process with a higher measurement accuracy.

The functional relationship between appropriately selected feature sets of samples and their permeation rates that were determined using a different measurement process can be determined, for example, by means of linear or non-linear regression, by means of a partial least square (PLS) algorithm, by means of a neuronal network, by means of a combination of at least two of these methods or of other regression methods (regression model).

The regression model that was prepared using the data sets of samples detected with the assembly in accordance with the invention that were subjected to the data reduction and the feature extraction and whose permeation rates—determined using a different measurement process—should be included in the electronic memory. The permeation rate of a comparatively investigated sample of the same sample class having a comparable structure can be determined from the data sets determined using the assembly in accordance with the invention using a regression model stored in the electronic memory.

The electronic evaluation unit carries out the data reduction and feature extraction of the data sets determined using the assembly in accordance with the invention. An evaluation of the spectral information and subsequently of the spatial information can take place first here. An order reversed with respect thereto or any desired combination of more than two individual steps for data reduction and feature extraction is also possible.

The data reduction and feature extraction can take place by means of principal component analysis (PCA), parameterization of texture information, averaging, and/or determination of the standard deviation and combinations thereof.

In the case of the use of principal component analysis, the n intensities of the wavelengths (spectra) of all the local points are transformed by coordinate transformation into a new orthogonal coordinate system—the principle component space—in which the original data have maximum variance, and with n representing the number of measured wavelengths.

The coordinate transformation is calculated by the determination of the n eigenvectors (principal components) and of the associated n eigenvalues of the covariance matrix of the data set of the measured part surface. The greater the nth eigenvalue, the more the corresponding nth principal component describes the original variance, i.e. the eigenvector having the greatest eigenvalue is the 1st principal component of the data set and describes the greater part of the original variance of the data set. The eigenvector having the lowest eigenvalue is the nth principal component of the data set and does not describe any relevant properties of the data set. Only a specific number of principal components are taken into account—frequently the first three to six that already ensure a sufficient description—for example >95%—of the original variance of the data set. The number of principal components—and thus the dimensionality of the principle component space—to be taken into account can be selected with criteria assistance, for example with reference to the proportion in the total variance or with reference to a screen test.

The coordinates of the spectra in the newly spanned principle component space are the so-called score values that sufficiently characterize the corresponding local point.

The data reduction and feature extraction can advantageously take place using the electronic evaluation unit such that the data detected in accordance with the invention are evaluated in the same manner as the data of the samples with reference to whose known permeation rates the regression model was prepared. The permeation rate of the sample is subsequently determined using the regression model by means of the data set detected in accordance with the invention, the intensities of the electromagnetic radiation detected with exact spatial and wavelength resolution.

The following procedure can preferably be used in the evaluation of the data detected in accordance with the invention:

Variant a) The first six principal components, including the score values, are preferably determined by a principal component analysis of the spectral information of all the local points of the part surface. Since the data detected in accordance with the invention represent all the local points of an investigated surface, the areal distribution of the score values per principal components can be specified. The quantification of the different areal distribution of the score values takes place here by different statistical parameters that are determined using all the score values of a principal component of the respective part surface. They are in particular the variance, the interquantile range, or the mean absolute deviation. This procedure can be used for all principal components. The determination of the permeation rate takes place by the electronic evaluation unit on the basis of a regression model such as a partial least square (PLS) regression model, where the parameters are optionally subjected to a further prior feature extraction, preferably via a further principal component analysis (PCA).

The regression model used here (PLS here) was determined beforehand using samples of the same sample class having a comparable structure whose permeation rates, in particular the water vapor transmission values, were determined using a different measurement method having a higher measurement accuracy, where all the steps of the feature extraction were carried out analogously to the above-described process.

Variant b) One or more principal components, in particular the score values of the local points per principal component, that can be specified distributed areally over the sample are calculated via a principal component analysis of the spectral information of all the detected local points of the respective investigated part surface. The local points can here be described by different parameters of the score values; in addition to the actual value also in particular by the threefold standard deviation from the mean value of all the score values of the respective part surface. If this parameter at a local point deviates by more than threefold the standard deviation from the mean value of this parameter of all the local points, it is classified as a defect. If such a local point is disposed next to a local point already classified as a defect, groups of local points classified as defects (defect regions) can be determined in this manner. The defect regions are divided into different groups for the further feature extraction and thus for determining the feature "permeation rate", with the group classification of the detect regions determined in accordance with the invention being able to take place by a determination of parameters that provide spatial information on the defect region, in particular on the area, the extent in the direction of both spatial coordinates, the center, the eccentricity, the equivalent diameter, the periphery length, the filling of the enveloping polygonal surface, and the ratio of the surface to the enveloping convex surface. The parameter sets describing the defects can be associated with specific defect types by means of a further classification process, advantageously by means of a cluster analysis, with a classification into four defect types having proved to be advantageous. The permeation rate per part surface can be determined from the number of defects per defect type that were determined on the sample with reference to a regression model, in particular to a linear regression model. The regression model used here was determined beforehand using samples of the same sample class having a comparable structure whose permeation rates, in particular the water vapor transmission values, were determined using a different measurement method having a higher measurement accuracy, where all the steps of the feature extraction were carried out analogously to the above-described process.

An investigated part region should have a size in the range 500 µm×500 µm up to 1500 µm×1500 µm. A detection should be able to be performed at a spatial resolution in the range 0.5 µm to 1.5 µm, preferably at 1 µm.

At least 30 detectors, preferably at least 100 detectors, should be arranged in a row here.

At least one detector, preferably at least 50 detectors, should be arranged in a column here.

An assembly in accordance with the invention can use an HSI camera having suitable beam-shaping optical elements and electronic evaluation electronics.

The irradiation of the surface should take place at at least an angle in the range 0° to <90° with respect to the normal of the surface of the sample. On an irradiation through a sample transparent for the electromagnetic radiation, the angle should advantageously be observed of at least almost 0° to the sample normal, that is the radiation should be directed onto the surface of the sample in as perpendicular a manner as possible to keep the reflected portion as small as possible. The irradiation and detection can also be carried out at a variable angle of incidence of the electromagnetic radiation. As already expressed, angles of incidence can be selected in the range of 0° to a maximum of 89° here. The detection can also be limited to linearly polarized electromagnetic radiation. In this case, an advantageous alignment of one or more polarization planes before and/or after the sample can be selected.

The detectors and the sample can in particular be moved along at least one axis relative to one another and in this respect preferably at an advantageous spacing from one another on a use of detectors that can only measure a line in a simultaneously spectral and spatially resolved manner. A sample can thus be moved along an axis with statically fixed detectors and radiation source. This can be achieved with a correspondingly movable table on which a sample is arranged that can be moved in an x direction and optionally also in a y direction. However, an unwinding from roll to roll is also possible when the sample is of flexibly deformable material, for example in the form of a film.

Elements shaping the electromagnetic radiation can be present at the radiation source. In a simple embodiment, the radiation source can be combined with a microscope. A radiation source can, however, also be arranged in a hollow body from which the electromagnetic radiation exits diffusely and can be directed to the surface to be irradiated. The hollow body can be a sphere or a cylinder. A surface to be detected simultaneously should be homogeneously irradiated. With a radiation source with beam-shaping optical elements, the utilized wavelength range should be taken into account in the selection of the respectively used optical elements serving the beam shaping.

A diaphragm that avoids the incidence of scattered electromagnetic radiation can preferably be arranged in front of the detectors in the optical beam path of the electromagnetic radiation.

Electromagnetic radiation whose wavelength range starts in the UV spectrum and ends in the IR spectrum can be emitted from the radiation source. Radiation from the wavelength range of visible light up to and into the NIR spectrum, that is from 250 nm to 1000 nm, is particularly preferred. Where possible, all the wavelengths within the respective interval should be able to be used for radiation in a utilized wavelength range. The limits should be predefined solely by the sensitivity range of the detectors used with respect to their sensitivity/measurement accuracy of the intensities detectable with them for the respective wavelengths and with respect to the optical properties of the beam guiding components. Those spectral ranges should preferably be used that have the greatest variance between the spectra of the samples of the target WVTR range and that have a determination error that is as small as possible.

At least one element with which a direct choice of the polarization of the electromagnetic radiation can be achieved can also be present in the optical path or can be integrated therein.

A sample can also be a multilayer design of a plurality of layers preferably formed from different materials or substances. The basic material of the sample is a polymer film or a thin metal film or glass film onto which further thin films of polymer, ceramics or metal can be applied in different combinations.

The detectors used and the electronic evaluation unit as well as optionally also the radiation source can represent a so-called hyper-spectral image system that can be used in the assembly in accordance with the invention. Spatial information for the respective detected part region of the sample can thereby also be obtained in addition to spectral information.

A reduction of the data that were determined on the detection of intensities determined at the individual local points for the individual wavelengths of a detected wavelength range (spectrum) can be advantageous in the actual evaluation. Information relevant to the determination of the permeation rate can thereby be separated from the non-relevant information, whereby the electronic processing effort is also substantially reduced and the required time is likewise reduced. The use of a highly complex, cost-intensive electronic processing technique is not required.

A statistical model can be prepared in the invention on whose basis the permeation rate of the investigated sample system in the correspondingly underlying part region can be predicted. For this purpose, the data set can be detected with one of a plurality of optical detectors which are preferably arranged in a row and with which a detection of intensities is possible with wavelength resolution and spatial resolution.

The value of the permeation rate is influenced by deviations from the ideal state of the sample. These deviations can be defective points, particles, layer thickness variations, material changes, etc. These artefacts equally have the effect that light that interacts with the sample is differently (spectrally, intensity) reflected, scattered, or transmitted. The totality of a sufficient number of individual intensities (spectra) of different local points of a detected part surface of a sample detected with wavelength resolution can thus represent the information on the permeation rate in the sample range under observation.

The permeation rate for the determination of the permeation rates can be determined with reference to a measured feature set using a regression model set up with feature sets having known permeation rates measured beforehand at samples of the same sample class having a comparable structure.

The measured feature sets are subjected to a data reduction and thus to a feature extraction for this purpose. The wavelength spectra detected at the individual local points of the respective part surface can thus be subjected to a spectral feature extraction, for example to a cluster analysis or a principle component analysis. The parameters used in the regression model can accordingly be the number and distribution of the clusters, the score values of the principle components, or their distribution.

Furthermore, methods of image compression can be used for a texture evaluation for the feature extraction, in which texture evaluation the intensities of individual wavelengths detected at all local points of the respective part surface or those of the sum or of the averaged sum of the intensities of a plurality of wavelengths, or the parameters determined by a spectral feature reduction and/or their combinations are subjected to an image compression. To describe the texture information of the data set, at least one parameter should be determined in this respect via a wavelet transformation or another image compression method such as Taylor polynomials, Fourier and cosine transformations, discrete cosine transformation, or gray value matrix method.

The permeation rate of part surfaces can be predicted on the basis of a calibration model (regression model) that was prepared using measured data sets of samples of the same sample class having a comparable structure and a known permeation rate, with the respective measured data sets being treated for the calibration and prediction using identical steps of the feature reduction. A "multiple linear regression analysis" (MLRA), a "principle component regression" (PCR), a "partial least square regression" (PLS), or a "neuronal network" can be used as a regression model by way of example here.

The requirements for a sufficient determination accuracy are a homogeneous illumination of the surface used for the detection so that a superposition of the intensity fluctuations caused by the sample with lateral fluctuations of the illumination intensity can be avoided by implementations of a laterally homogeneous light field. A microscope optics can advantageously be used for small sample regions. The assembly in accordance with the invention can be adapted to the respective surface of the sample to be detected by use of different optics, working distances, and enlargements.

A determination of permeation rates of samples can be carried out using the invention within a few milliseconds to minutes instead of days or months. A contactless measurement is possible. The samples do not have to be additionally treated or otherwise prepared. A use in quality control and in inline monitoring of production is preferred so that no sample removal and no separate determination are required in these cases.

The invention can advantageously be used for the determination of the barrier properties and permeation properties of strong barrier materials. They are in particular used in the packaging industry, in the coating of LCD panels/TFTs, in the encasing/encapsulation of thin film solar cells, or for a secure OLED encapsulation.

The invention will be explained in more detail by way of example in the following.

Example 1

A sample of polyethylene terephthalate film (thickness of approximately 75 μm) that has been coated with tin-zinc oxide having a layer thickness of approximately 150 nm was homogeneously irradiated over a selected surface of 5 mm×6 mm using a halogen lamp as a light source while using an optical microscope and was divided into 30 part surfaces. A total of 1000×50 optical detectors were arranged in a row and column assembly above the sample so that the total sample surface could be detected with wavelength resolution and spatial resolution over a width of 5 mm. A detection of the intensities of the light reflected by the sample with wavelength resolution was implemented for individual local points using the optical detectors. A total of 50 wavelengths in the range from 400 nm to 1000 nm was taken into account. The sample here was moved perpendicular to the row assembly of the detectors to detect the total sample surface.

The intensities detected with wavelength resolution by the detectors for the individual local points were associated with part regions of the sample each having a size of 1 mm×1 mm. Such part regions having two lateral dimensions and one spectral dimension can also be called a hypercube.

A data reduction in which the procedure as described below was followed subsequently took place for the respective part region:
1. Mean value smoothing of the spectra Removal of noise from the measured spectra.
2. Principal component analysis of the hypercube of the part region A reduction of the dimensionality of the data is thereby achieved without important information being lost.
3. Calculation of the variance, of the interquantile range, and of the mean absolute deviation of the eigenvalues of every single principal component. The result is a set of different features.

Variance ($\sigma^2$):

$$\sigma^2 = \frac{\sum_{i=1}^{n}(x_i - \bar{x})^2}{n-1}$$

Where $x_i$=eigenvalue i $\dot{x}$ mean value of the eigenvalues
Interquantile Range (IQR):

$IQR = Q_{0.75} - Q_{0.25}$ $Q_{0.75/0.25}$ ... 75% and 25% quantile
Mean Absolute Deviation (e):

$$e = \frac{1}{n}\sum_{i=1}^{n}|x_i - \bar{x}|.$$

n=number of eigenvalues of the image
4. A determination of the permeation rate of the investigated sample took place using the regression model prepared beforehand while using data sets of part surfaces having known permeation rates and with a data treatment analog to that described in steps 1-4, said regression model being stored in the electronic memory of the electronic evaluation unit.

The invention claimed is:
1. An assembly for determining the permeation rate of a sample for at least one permeate, in particular water vapor, in which a plurality of detectors that are configured for a spatially resolved spectral analysis of electromagnetic radiation within a wavelength interval are arranged in a row arrangement or in a row and column arrangement; and
the detectors are connected to an electronic evaluation unit and are arranged such that electromagnetic radiation emitted by a broadband radiation source impacts the detectors either after reflection at the surface of the sample, at a layer formed on the sample or at the surface of a layer within the sample and/or after the irradiation of a sample transparent for the electromagnetic radiation; wherein
the irradiation takes place such that an intensity of the electromagnetic radiation that is homogeneous laterally and in time is observed on a surface from which the electromagnetic radiation is reflected or which is transmitted by the surface; and
the electronic evaluation unit is configured such that the measured signals of the detectors detected with spatial resolution and wavelength resolution can be detected within a wavelength interval for individual local points that are arranged on a predefinable surface of the sample and in so doing measured signals detected at a plurality of positions can be associated with a respective part region of the detected surface (hypercube); and
a data reduction in which significant features are selected can be carried out for all measurement signals of the part regions of the detected surface detected with wavelength resolution; and
a statement on a corresponding permeation rate can be achieved with reference to these selected features using a regression model determined beforehand and stored in an electronic memory, said regression model having been prepared using the feature sets of samples obtained in an analog manner whose permeation rates were determined using a different measurement method that has a higher measurement accuracy.

2. An assembly in accordance with claim 1, characterized in that the electronic evaluation unit is configured such that a data reduction can be achieved by feature extraction by means of principal component analysis, extraction of texture information, mean value formation, determining the standard deviation and/or combinations thereof.

3. An assembly in accordance with claim 1, characterized in that an investigated part region has a size in the range 500 µm×500 µm to 1500 µm×1500 µm.

4. An assembly in accordance with claim 1, characterized in that the irradiation of the surface takes place at least one angle in the range 0° to <90° with respect to the normal of the surface of the sample.

5. An assembly in accordance with claim 1, characterized in that the detection and evaluation can be carried out using at least one polarizer having at least one defined known polarization plane with respect to the plane of incidence.

6. An assembly in accordance with claim 1, characterized in that the detectors and the sample are movable along at least one axis relative to one another and in so doing preferably at a constant spacing from one another.

7. An assembly in accordance with claim 1, characterized in that the radiation source has optical elements forming the electromagnetic radiation or a radiation source that emits an electromagnetic radiation diffusely over the surface, and that is in particular arranged within a hollow body and a diaphragm that avoids the incidence of scattered electromagnetic radiation is particularly preferably arranged in front of the detectors in the optical path of the electromagnetic radiation.

8. An assembly in accordance with claim 1, characterized in that the sample has a multilayer structure that is preferably formed with a plurality of layers formed from different materials or substances.

9. An assembly in accordance with claim 1, characterized in that the row and column arrangement of detectors is formed by optical elements and evaluation electronics using an HSI camera.

* * * * *